United States Patent [19]

Handa et al.

[11] 4,251,225
[45] Feb. 17, 1981

[54] METHOD OF DETECTING CARBON MONOXIDE

[75] Inventors: Takashi Handa, Kamakura; Koichi Endo, Inagi, both of Japan

[73] Assignee: Nohmi Bosai Kogyo Co., Ltd., Tokyo, Japan

[21] Appl. No.: 62,513

[22] Filed: Jul. 27, 1979

Related U.S. Application Data

[63] Continuation-in-part of Ser. No. 885,013, Mar. 9, 1978, abandoned.

[30] Foreign Application Priority Data

May 19, 1977 [JP] Japan .................................. 52-57117

[51] Int. Cl.$^3$ ........................ G01N 27/04; H01B 1/08
[52] U.S. Cl. ..................................... 23/232 E; 73/23; 252/514; 338/34; 422/98
[58] Field of Search ................. 23/232 E; 422/88, 90, 422/94, 95, 98; 338/13, 22 SD, 34; 324/71 SN; 73/23 (U.S. only), 27 R (U.S. only); 252/408, 514 (U.S. only)

[56] References Cited

U.S. PATENT DOCUMENTS

| | | | |
|---|---|---|---|
| 3,865,550 | 2/1975 | Bott et al. | 422/98 X |
| 4,030,340 | 6/1977 | Chang | 422/98 X |
| 4,033,169 | 7/1977 | Fujishiro et al. | 422/96 X |

OTHER PUBLICATIONS

German Publication, Offenlegungsschrift 2636178, Mar. 3, 1977.

*Primary Examiner*—Joseph Scovronek
*Attorney, Agent, or Firm*—Wenderoth, Lind & Ponack

[57] ABSTRACT

Method of detecting carbon monoxide gas at temperatures of 100° C. or less by using a detecting element containing stannic oxide as the main component, which element is prepared by mixing stannic oxide, antimony trioxide and platinum in atomic ratios of Sb/Sn = at least 0.005, Pt/Sn = at least 0.004 and Sb/Pt = at least 0.005, and sintering said mixture at a temperature of at least 625° C.

2 Claims, 1 Drawing Figure

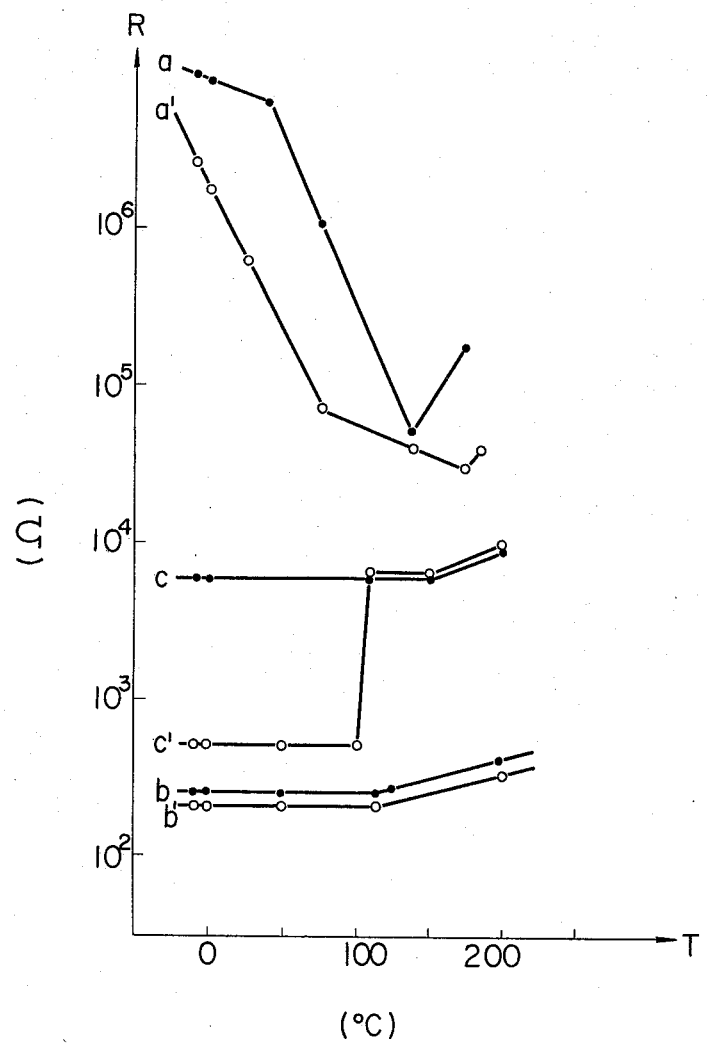

METHOD OF DETECTING CARBON MONOXIDE

CROSS-REFERENCE TO RELATED APPLICATION

This application is a continuation-in-part application of Ser. No. 885,013, filed Mar. 9, 1978, now abandoned.

BACKGROUND OF INVENTION

This invention relates to the use of an improved gas detecting element which selectively detects only carbon monoxide from among various reducing gases in air.

It has already been known to use a metallic oxide semi-conductor containing stannic oxide, $SnO_2$, as the main component for a reducing gas detecting element. The concentration of the gas is detected by utilizing the change in resistance of this element caused by the adsorption of the gas.

However, the above-mentioned conventional element responds to various gases, and furthermore, it must be heated to a high temperature of about 250° C. when in use. Thus, due to the lack of selectivity, and the high consumption of electric current, the conventional element is quite unsuitable for use in a gas alarm which is required to respond only to a specific gas, or which is required to be continuously used.

In order to overcome this drawback, there has been proposed an $SnO_2$-Pt type gas detecting element prepared by adding platinum, Pt, to stannic oxide, $SnO_2$, as a catalyst, which element selectively responds to carbon monoxide gas and works at a relatively low temperature (see Japanese Patent Laid Open No. 50-17287). However, even with regard to this element, the resistance of the element varies in accordance with the change in temperature of the element, and therefore it is necessary to provide a subsidiary circuit in order to maintain a constant temperature of the element. Besides, it is necessary to use the element at a temperature of about 70° C. or higher in order to amplify the resistance change caused by the adsorption of gas.

SUMMARY OF INVENTION

It is an object of this invention to provide a method of detecting carbon monoxide gas having a temperature ranging from −10° to 100° C., by using a carbon monoxide gas detecting element which can detect carbon monoxide gas when the temperature of the element is within this temperature range.

We have found, as a result of a study in view of the above-mentioned problems, that an improved element, the resistance of which is not substantially influenced by temperature, and which exhibits no loss of the selective response to only carbon monoxide gas, can be obtained by adding antimony, Sb, to an $SnO_2$-Pt type gas detecting element. In addition, this gas detecting element can be produced with an addition of platinum as a catalyst in a smaller amount than before.

BRIEF DESCRIPTION OF DRAWING

In the drawing, the vertical axis R represents the resistance value (Ω) of a detecting element, and the horizontal axis T represents the temperature value (°C.) of the element.

DETAILED DESCRIPTION OF INVENTION

The following three types of gas detecting elements were prepared for the purpose of comparison:

(a) An $SnO_2$-Pt type gas detecting element prepared by mixing 1 g of stannic oxide, $SnO_2$, with 1 ml of 0.26 N chloroplatinic acid, $H_2PtCl_6$ (as a catalyst), coating the resultant mixture on a porcelain tube and sintering the coating at 850° C. in air;

(b) An $SnO_2$-$Sb_2O_3$ type gas detecting element prepared by mixing 10 g of stannic oxide, $SnO_2$, with 100 mg of antimony trioxide, $Sb_2O_3$, coating the resultant mixture on a porcelain tube and sintering the coating in the same manner as above; and (c) An $SnO_2$-$Sb_2O_3$-Pt type gas detecting element of this invention prepared by mixing 10 g of stannic oxide, $SnO_2$, 100 mg of antimony trioxide, $Sb_2O_3$, and 10 ml of 0.26 N chloroplatinic acid, $H_2PtCl_6$ (as a catalyst), coating the resultant mixture on a porcelain tube and sintering the coating in the same manner as above.

The relationship between the temperature and the resistance value of each of the above prepared gas detecting element samples was measured and the result is shown in the accompanying drawing.

Curve (a) in the drawing shows the property of $SnO_2$-Pt type gas detecting element (a) measured in air, while curve (a') shows that measured in air containing 1000 ppm of carbon monoxide gas. As can be seen from these curves, the resistance decreases as the temperature increases in both the atmosphere of air and that containing carbon monoxide gas. In the vicinity of about 170° C., the property of the element becomes close to that of metal and the resistance increases. Therefore, in the case of this conventional element, it is necessary to provide a subsidiary circuit in order to maintain a constant temperature of the element.

Curve (b) shows the property of $SnO_2$-$Sb_2O_3$ type gas detecting element (b) measured in air, while curve (b') shows that measured in air containing 1000 ppm of carbon monoxide gas. As can be seen from these curves, the resistance of the element is constant and produces a flat curve at a temperature of the element ranging from −10° to 100° C. This is due to the presence of antimony, Sb, in the element. However, since this element does not contain platinum, Pt, a change in the resistance does not appear even when the element adsorbs carbon monoxide gas.

Curve (c) shows the property of $SnO_2$-$Sb_2O_3$-Pt type gas detecting element (c) of this invention measured in air, while curve (c') shows that measured in air containing 1000 ppm of carbon monoxide gas. As can be seen from these curves, the resistance of the element is constant and produces a flat curve at a temperature ranging from −10° to 100° C., and the resistance change caused by the adsorbed carbon monoxide gas sufficiently appears due to the presence of added platinum, Pt.

Although the above tests were carried out in an atmosphere containing 1000 ppm of carbon monoxide gas, we have found that the gas detecting element used in the present invention can constantly detect carbon monoxide gas present in amounts as low as 50 ppm.

We have tested the various properties of the $SnO_2$-$Sb_2O_3$-Pt type gas detecting element of this invention by varying the ratios of the components. As a result of this test, we have noted the following facts:

(1) If the atomic ratio of Pt/Sn is at least 0.004, the selective response to only carbon monoxide gas can be obtained.

(2) If the ratio of Sb/Sn is at least 0.005, the resistance of the element is not substantially influenced by the temperature of the element.

(3) If the ratio of Sb/Pt is at least 0.005, the evaporation of platinum added in the form of an acid or salt to stannic oxide can be avoided and the formation of platinum as a catalyst becomes easy, thus reducing the amount of platinum necessary to be added in the form of acid or salt. This is proved by the fact that when an $SnO_2$-Pt type element containing no antimony is sintered on an alumina boat, the color of the boat turns grey-black due to the evaporation of platinum. On the other hand, in the case of sintering an element having antimony added on an alumina boat, the boat retains its white color, thus proving that platinum is sintered together with stannic oxide without evaporating, and is converted to a platinum catalyst.

Preferably, from an economic point of view, the upper limits of the ratios of the various components of the element should be such that Sb/Sn is 0.005–0.1, Pt/Sn is 0.004–0.2, and Sb/Pt is 0.005–5.

The preparation of the $SnO_2$-$Sb_2O_3$-Pt type gas detecting element of this invention is fully illustrated by the following examples.

EXAMPLE 1

10 g of stannic oxide, $SnO_2$, is mixed with 80 mg of antimony trioxide, $Sb_2O_3$ in a mortar for 30 minutes. 1 g of the resultant mixture is mixed with 1 ml of 0.26 N chloroplatinic acid, $H_2PtCl_6$, and the mixture is dried naturally. The dried mixture is then converted into a paste-like material with the addition of distilled water. The resultant paste-like material is coated on an alumina porcelain tube, and is dried at 50° C. for 30 minutes. Thereafter, the dried coating is sintered at 800° C. for 30 minutes.

EXAMPLE 2

1 g of stannic oxide, $SnO_2$, is mixed with 1 ml of 0.26 N chloroplatinic acid, $H_2PtCl_6$, and the mixture is dried naturally. The mixture is then coated on an alumina procelain tube, and is dried at 50° C. for 30 minutes. This porcelain tube is placed on a boat, and 0.1 g of antimony trioxide, $Sb_2O_3$, is placed in the bottom of the boat. The contents of the boat are then sintered for 1 hour at 650° C. which is close to the melting point of antimony trioxide, $Sb_2O_3$, (625° C.).

As explained above, the resistance of the gas detecting element of this invention remains constant at temperatures in the range of $-10°$ to 100° C. Consequently, it is not necessary to use a heater to heat the element or a subsidiary circuit to keep the temperature constant. Also, the element of this invention shows a constant resistance change in accordance with the presence of carbon monoxide gas, even if it is left at normal temperature for a long period of time. Accordingly, this invention provides for the use of an excellent gas detecting element which is selectively responsive to carbon monoxide gas and is suitable for use in a gas alarm.

As indicated above, the resistance of the present gas detecting element is changed by the adsorption and desorption of carbon monoxide gas. Employing this phenomenon, the manner in which the element is used will be apparent to those skilled in the art. For example, the element can be electrically connected to a current detection means which activates a signal means when the current flowing to the current detection means changes. The present invention does not reside in the particular manner in which the element is used, but rather, resides in the use of this particular element to detect carbon monoxide gas at a temperature from $-10°$ to 100° C. For this purpose, the element is merely placed in an atmosphere in which the possible presence of carbon monoxide is to be detected, the element being included in an electrical circuit which also includes a signal means responsive to the change in electrical resistance of the element which occurs when carbon monoxide in the atmosphere contacts the element.

We claim:

1. A method of detecting carbon monoxide gas at a temperature of from $-10°$ to 100° C., by using, as the only carbon monoxide gas detecting element, an element consisting of stannic oxide as the main component, antimony, and platinum, which element is prepared by mixing stannic oxide, antimony trioxide and platinum in atomic ratios of Sb/Sn=at least 0.005, Pt/Sn=at least 0.004 and Sb/Pt=at least 0.005, and sintering said mixture at a temperature of at least 625° C.

2. A method according to claim 1, wherein said atomic ratios are Sb/Sn=0.005–0.1, Pt/Sn=0.004–0.2 and Sb/Pt=0.005–5.

* * * * *